United States Patent [19]

Hurley et al.

[11] Patent Number: 4,870,025
[45] Date of Patent: Sep. 26, 1989

[54] METHOD OF SENSING METHANE GAS-I

[75] Inventors: Michael D. Hurley, Ann Arbor; William J. Kaiser, Farmington Hills; Eleftherios M. Logothetis, Birmingham, all of Mich.

[73] Assignee: Ford Motor Company, Dearborn, Mich.

[21] Appl. No.: 781,579

[22] Filed: Sep. 30, 1985

[51] Int. Cl.$^4$ .......................................... G01N 25/22
[52] U.S. Cl. ..................... 436/141; 436/157; 436/159; 436/160; 436/158; 422/94; 422/95; 422/96; 422/97; 73/25; 73/26; 73/27 R
[58] Field of Search ............ 422/94, 95, 96, 97; 436/141, 155, 157, 159, 160, 158; 73/25, 26, 27 R; 324/71.1, 71.5

[56] References Cited

U.S. PATENT DOCUMENTS

| | | | |
|---|---|---|---|
| 2,514,690 | 7/1950 | Bliss et al. | 430/31 |
| 2,857,251 | 10/1958 | Krozh | 436/30 |
| 2,904,406 | 9/1959 | Moore | 422/94 |
| 2,955,922 | 10/1960 | Christy | 422/96 |
| 4,063,898 | 12/1977 | Fisher | 422/94 |
| 4,298,573 | 11/1981 | Fujishiro | 73/26 |

FOREIGN PATENT DOCUMENTS

| | | | |
|---|---|---|---|
| 2834671 | 4/1979 | Fed. Rep. of Germany | 324/71.5 |
| 536059 | 5/1941 | United Kingdom | 422/96 |

*Primary Examiner*—Barry S. Richman
*Assistant Examiner*—L. Kummert
*Attorney, Agent, or Firm*—William E. Johnson; Clifford L. Sadler

[57] ABSTRACT

A method of selectively sensing the quantity of methane gas in an oxygen containing gas stream, which method, as taught in one of its preferred embodiment, includes the step of providing a platinum catalyst (12) and a palladium catalyst (14). The platinum and the palladium catalysts are electrically interconnected (16—16) so as to obtain an electrical output reading (24) therefrom. The electrically interconnected catalysts are heated to a temperature in a range of 350°–450° C. whereby a reference electrical output reading is obtained therefrom. A gas stream containing suspected methane is passed over the electrically interconnected catalysts. Methane gas contained in the gas stream is oxidized only by the palladium catalyst while all other oxidizable components of the gas stream are oxidized by both catalysts. In this manner, the palladium catalyst will be heated to a temperature proportionately higher than the platinum catalyst based on the percentage of methane gas contained in the gas stream. A sample measuring electrical output reading is obtained from the electrically interconnected catalysts while the suspected methane containing gas stream is passing thereover. The sample measuring electrical output reading is compared to the reference electrical output reading to determine the percentage of methane gas contained in the gas stream.

5 Claims, 1 Drawing Sheet

METHOD OF SENSING METHANE GAS-I

TECHNICAL FIELD

This application is directed to a method of sensing methane gas and, in particular, to a method of selectively and quantitatively sensing methane gas in an oxygen containing gas stream. The presence of hydrocarbons other than methane does not interfere with the methane generated response.

BACKGROUND AND PRIOR ART STATEMENT

There is need in industry for a method of sensing methane which is quantitative and selective to methane in the presence of other hydrocarbons. Methane is a highly explosive gas and thus the presence of methane in excessive amounts must be detected so that proper preventive measures may be followed.

It has been proposed, for example, to power motor vehicles with methane as the fuel. Thus, a garage in which the methane burning vehicle is parked would need a methane sensor, as would the area of the vehicle where the methane was stored. Additional places where methane sensors are of value are in mines where the accumulations of methane often can result in explosions and loss of human life. Additionally, methane sensors can be used in laboratory instruments to quantitatively detect the presence of methane specifically and the amount of material present.

The method of our invention is simple, inexpensive to use, and based on the reaction of catalysts to the constituents in an oxygen containing gas stream. The method identifies the presence of methane specifically and identifies the amount of material that is present.

A prior art search was conducted in the U.S. Patent & Trademark Office on the subject matter of this invention disclosure by Mr. M. D. Hurley, one of the inventors of the method of this specification. Mr. Hurley's search uncovered the following patents:

U.S. Pat. No. 3,595,621 issued on Jul. 27, 1971 for a "Catalytic Analyzer".

U.S. Pat. No. 4,045,177 issued on Aug. 30, 1977 for an "Apparatus for Detecting Combustible Gases."

U.S. Pat. No. 4,063,898 issued on Dec. 20, 1977 for a "Combustible Gases Detector."

U.S. Pat. No. 4,164,539 issued on Aug. 14, 1979 for a "Catalytic Gas Detector."

U.S. Pat. No. 4,170,455 issued on Oct. 9, 1979 for a "Gas Monitoring Method and Apparatus Therefor."

These patents and their relationship to the subject matter disclosed and claimed in this application will be set forth briefly below.

U.S. Pat. No. 3,595,621 is directed to a gas analysis technique and method of detecting the presence of certain constituents of a gas. A filament having a high thermal coefficient conductivity is coated with an oxide catalyst and positioned in a gas stream to be analyzed. A heater supplies heat to the stream as it passes to the catalyst coated filament and maintains the stream at temperatures at which the components of the stream to be detected react in the presence of the catalyst. Detecting elements coated with selective catalysts and made of tungsten filaments are disclosed. The method disclosed in this patent does not use a platinum and a palladium catalyst, as will be explained in greater detail hereinbelow, to selectively sense the quantity of methane gas present in an oxygen containing gas stream.

U.S. Pat. No. 4,045,177 is directed to an improved apparatus for detecting combustible gases such as methane. The apparatus embodies a Wheatstone bridge circuit including a refractory coated reference element constituting one leg of the bridge and a refractory coated detector element having thereon a catalyst for promoting oxidation of the combustible gases to be detected constituting a second leg of the bridge. The specification mentions that the one leg of the bridge which forms the reference element may be formed of platinum wire, but the wire is completely coated with a refractory material so as to protect the same. Upon oxidation of combustible gas at the detector element, the temperature and resistance thereof increases relative to the reference element to unbalance the bridge, thereby producing an electrical signal proportional to the amount of combustible gas being oxidized. Once again, this patent does not teach the use of a platinum and palladium catalyst in combination to selectively sense the presence and quantity of methane gas.

U.S. Pat. No. 4,063,898 discloses a differential thermocouple combustible gas detector which is manufactured by providing a coating on one thermocouple junction of a differential thermocouple pair with a catalyst and the other thermocouple junction with a noncatalyst. Heated combustible gases react with the catalyst to liberate heat to the catalyst coated thermocouple junction in proportion to the concentration of combustible gases and proportionately raise the temperature of that junction above the noncatalyst coated junction. The output signal from the differential thermocouple device is thus a signal indicative of the concentration of combustible gases. Once again, this device does not selectively measure the quantity and presence of methane gas using platinum and palladium catalyst materials.

U.S. Pat. No. 4,164,539 discloses a catalytic gas detector which is formed as a sandwich and comprises two flat printed film resistance thermometer sensors back-to-back with a layer of thermally insulating material between them. A coating of a suitable catalytic substance is disclosed which covers an exposed flat face of one of the two sensors. Again this patent does not disclose a selective methane sensor based on the use of platinum and palladium catalysts forming a part of the detector.

U.S. Pat. No. 4,170,455 discloses a method and apparatus for monitoring the concentration of a component of a gas stream. The gas stream to be monitored is heated to a desired temperature and passed through an insulated gas passageway of a conduit member. The heated gas passes sequentially through a perforate metal shield and a body of particulate catalyst. The temperature of a heated gas entering and leaving the conduit member is monitored and any increase in temperature is corrolatable with the component concentration in the gas stream. The method and apparatus are particularly suitable for monitoring the concentration of hydrogen or oxygen in a gas stream. Once again, the method and apparatus disclosed is not one which is selective to the measurement of methane gas nor does it teach the use of platinum and palladium catalysts in order to obtain this selectivity.

DISCLOSURE OF INVENTION

This invention is directed to a method of sensing methane gas and, more particularly, to a method of selectively sensing the quantity of methane gas in an oxygen containing gas stream.

In accordance with the broad teachings of the method of our invention, the method is carried out in the following manner. A platinum catalyst is provided. A palladium catalyst is provided. The platinum and the palladium catalysts are electrically interconnected so as to obtain an electrical output reading therefrom. The electrically interconnected catalysts are heated to a temperature in a range of 350°–450° C. whereby a reference electrical output reading is obtained therefrom. The gas stream to be analyzed is passed over the electrically interconnected catalysts. Methane gas contained in the gas stream is oxidized only by the palladium catalyst while all other oxidizable components of the gas stream are oxidized by both catalysts. In this manner, the palladium catalyst will be heated to a temperature proportionately higher than the platinum catalyst based on the percentage of methane gas contained in the gas stream. A sample measuring electrical output reading is obtained from the electrically interconnected catalysts while the suspected methane containing gas stream is passing thereover. The sample measuring electrical output reading is compared to -the- reference electrical output reading to determine the percentage of methane gas contained in the gas stream.

In accordance with one preferred embodiment of the method of this invention, the method of selectively sensing the quantity of methane gas in an oxygen containing gas stream is carried out in the following manner. A platinum catalyst is provided. A palladium catalyst is provided. The platinum and palladium catalysts are interconnected in a series electrical connection. An electrical potential is applied to the interconnected catalysts to obtain an electrical output reading therefrom. The electrically interconnected catalysts are heated to a temperature in a range from 350°–450° C. whereby a reference electrical output reading is obtained therefrom. The gas stream containing the suspected methane is passed over the interconnected catalyst. Methane gas contained in the gas stream is oxidized only by the palladium catalyst while all other oxidizable components of the gas stream are oxidized by both components. In this manner, the palladium catalyst will be heated to a temperature proportionately higher than the platinum catalyst based on the percentage of methane gas contained in the gas stream. A sample measuring electrical output reading is obtained from the electrically interconnected catalyst while the suspected methane containing gas stream is passing thereover. The sample measuring electrical output reading is compared to the reference electrical output reading to determine the percentage of methane gas contained in the gas stream.

In accordance with still another preferred embodiment of the method of our invention, a method of selectively sensing the quantity of methane gas in an oxygen containing gas stream is carried out in the following manner. A high thermoelectric material having a high temperature resistance is provided. A first area of the high thermoelectric material is coated with a platinum catalyst. A second area of the high thermoelectric material spaced from and separate from the first area is coated with a palladium catalyst. The platinum and the palladium catalysts on the thermoelectric material are electrically interconnected so that an electrical output reading is obtainable therefrom. The electrically interconnected catalysts are heated to a temperature in a range of 350°–450° C. whereby a reference electrical output reading is obtained therefrom. The gas stream containing the suspected methane gas is passed over the electrically interconnected catalysts. Methane gas contained in the gas stream is oxidized by only the palladium catalyst while all other oxidizable components of the gas stream are oxidized by both catalysts. In this manner, the palladium catalyst will be heated to a temperature proportionately higher than the platinum catalyst based on the percentage of methane gas contained in the gas stream. A sample measuring electrical output reading is obtained from the electrically interconnected catalyst while the suspected methane containing gas stream is passing thereover. The sample measuring electrical output reading is compared to the reference electrical output reading to determine the percentage of methane gas contained in the gas stream.

BRIEF DESCRIPTION OF THE DRAWINGS

The novel features that are considered characteristic of the method of our invention are set forth with particularity in the appended claims. The invention itself, however, both as to its organization and its method of operation, together with additional objects and advantages thereof, will best be understood from the following description of specific embodiments when read in connection with the accompanying drawings, wherein like reference characters indicate like parts throughout the several figures, and in which:

BEST MODE AND INDUSTRIAL APPLICABILITY

The following description is what we consider to be a disclosure of preferred embodiments of the method of selectively sensing the quantity of methane gas in an oxygen containing gas stream in accordance with our inventive method. The following description also sets forth what we now contemplate to be the best modes of carrying out our inventive method. The description is not intended to be a limitation upon the broader principles of the method of our invention and while certain materials are mentioned, it does not mean that other materials cannot be used to carry out the method of our invention except in those situations where the materials are stated to be critical.

Figure 1:
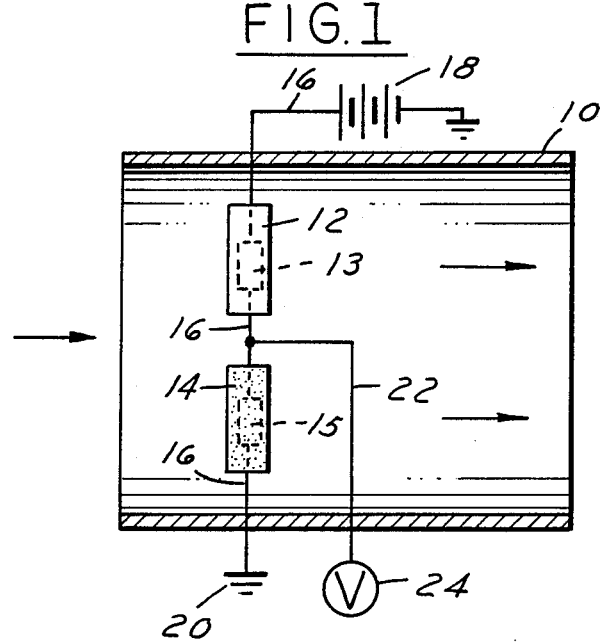
FIG. 1 is a schematic drawing of an environment in which a preferred method of our invention can be carried out.

In FIG. 1 there is schematically disclosed a structure for carrying out a preferred embodiment of the method of our invention. Our method is one of selectively sensing the quantity of methane gas in an oxygen containing gas stream. An oxygen containing gas stream with suspected methane contained therein is moved through a suitable conduit 10 from left to right as viewed in FIG. 1. A platinum catalyst 12 placed on a suitable thermistor 13 and a palladium catalyst 14 placed on a suitable thermistor 15 are mounted within the conduit 10 by suitable mounting structure not shown. The catalyst materials may be dispersed on suitable support bases on top of their respective thermistors in a manner well known to skilled artisans. For example, the catalyst material may be dispersed on alumina support material on top of their respective thermistors.

The platinum catalyst 12 and palladium catalyst 14 are electrically interconnected through their respective thermistors 13 and 15 in series connection by means of leads 16—16 to a suitable source of power 18 and ground 20. A lead 22 is connected to lead 16 between the platinum and palladium catalysts and is also connected to a device 24 for giving an electrical output reading. The thermistors for the platinum and palladium catalysts are generally designed so that the resistance thereof is equal under normal operating conditions when methane gas is not present. In such a situation, the device 24 will normally indicate a balanced electrical condition existing between the platinum and palladium catalysts and thus give a reference electrical output reading.

The platinum and palladium catalysts are heated to a temperature in a range from 350°–450° C. The 450° C. is not to be exceeded because above this temperature range the catalysts are not selective, as will be explained below, as they are within this temperature range. Thus, normal operating conditions are ones in which the catalysts are heated to the proper temperature range and at this proper range with inert gas or nonmethane containing gas stream flowing therethrough, a reference signal will be obtained on the device 24 which in essence is a reference signal indicating that the system is not detecting any methane passing therethrough. While no heating device is shown in the drawings, such heating devices are well known in the art. For example, the thermistors are heating devices incorporated into the platinum catalyst 12 and palladium catalyst 14. Additionally, the incoming gas stream may be heated to this temperature range by an auxiliary heating device in order to keep the system at the proper temperature. In another form, the entire conduit 10 may be enclosed in a heating device and the required heat supplied to maintain the system at the proper temperature. The last two cases would apply if the platinum catalyst and palladium catalyst were in the form of wire resistors and no thermistors were present.

The gas stream containing the suspected methane is passed over the interconnected platinum catalyst 12 and palladium catalyst 14. At the temperature range in consideration, any methane gas contained in the gas stream is only oxidized by the palladium catalyst 14. All other oxidizable components of the gas stream are equally oxidized by both the platinum catalyst 12 and the palladium catalyst 14. In this manner, the palladium catalyst 14 and associated thermistor 15 will be heated to a temperature proportionately higher than the platinum catalyst 12 based on the percentage of methane gas contained in the gas stream. Since the palladium is heated to a higher temperature, the resistance of its thermistor increases. Since there is an increase in resistance, the voltage drop over the catalyst changes and the reading on the device 24 is altered.

In this manner, a sample measuring electrical output reading is obtained from the device 24 while the suspected methane containing gas stream is passing over the interconnected catalyst. The change in the reading, of course, is a comparison between the sample measuring electrical output reading and the reference electrical output reading. The change therefore determines both the fact that methane gas is there in the oxygen containing gas stream and the percentage of methane gas based upon the signal on the device 24. The more methane gas present, the higher the temperature generated over the palladium catalyst 14, the higher resulting resistance of the palladium catalyst, and the greater reading on the device 24 from the reference electrical output reading obtained therefrom during conditions in which no methane was present in the system.

The whole thing which makes the method of this invention work is the fact that platinum will oxidize all oxidizable components of the gas stream with the sole exception of methane in this temperature range, while palladium will oxidize all of the oxidizable components of the gas stream in this temperature range including methane. The differential catalyst system therefore is one in which one catalyst is played off against the other catalyst so that the only component not oxidized by both is the methane, and thus if there is an imbalance in the system, it indicates not only that methane is present but that the degree of imbalance indicates the amount of methane present.

Figure 2:
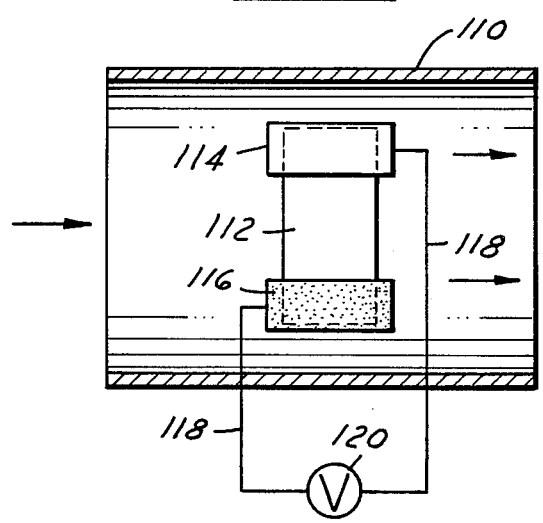
FIG. 2 is a schematic drawing of an environment in which still another preferred embodiment of the method of our invention can be carried out.

In FIG. 2 there is schematically shown apparatus for carrying out another embodiment of the preferred method of our invention for selectively sensing the quantity of methane gas in an oxygen containing gas stream. Once again the gas stream is moving through a suitable conduit 110 from left to right. In this case, a high thermoelectric material 112 having a high thermal resistance is provided. The high thermoelectric material is a conducting material in the form of a bar or an appropriate film on a suitable substrate. One material which is of value is a Nb-doped titanium dioxide. A first area of the high thermoelectric material is coated with a platinum catalyst 114. A second area of the high thermoelectric material spaced from and separate from the first coated area is coated with a palladium catalyst 116. Electrical leads 118—118 interconnect electrically the platinum and the palladium catalyst to a device 120 which can measure an electrical output between the catalysts.

In this particular case, the thermoelectric material 112 is a material which if heated differentially will pass electrons therethrough. Thus, if one end of the material is hotter than the other end thereof, electrons will flow toward the cold end of the material. The resulting difference in the electron concentrations at the two ends of the material will generate a thermoelectric EMF between the two ends. The greater the differential in temperature the more electrons will flow and thus the greater the voltage that is developed.

The high thermoelectric material 112 having the platinum catalyst 114 and palladium catalyst 116 is heated by suitable means, as previously described in connection with FIG. 1, to a temperature of 350-450° C. At such a temperature and with no methane containing atmosphere flowing over the device, there is no temperature difference between the opposite ends of the thermoelectric material. Thus, there will be no thermoelectric voltage generated therebetween and a reference electrical output reading is obtained on the device 120.

A gas stream containing suspected methane gas is passed over the electrically interconnected catalysts 114 and 116. The methane gas contained in the gas stream is oxidized by only the palladium catalyst 116 while all other oxidizable components of the gas stream are oxidized by both catalysts. In this manner, when the gas stream contains methane, the palladium catalyst 116 will be heated to a temperature proportionately higher than the platinum catalyst 114 based on the percentage of methane contained in the gas stream. The higher temperature, of course, heats one end of the high thermoelectric material 112 to a higher temperature and will therefore generate a thermoelectric voltage. This will result in the generation of an EMF based upon the magnitude of the methane contained in the atmosphere which generates the temperature difference. Thus, a reading is obtained on the device 120 which is a sample measuring electrical output from the electrically interconnected catalyst. This sample measuring electrical output reading is compared to the reference electrical output reading to determine the percentage of methane gas contained in the gas stream.

While particular embodiments of the invention have been illustrated and described, it will be obvious to those skilled in the art that various changes and modifications may be made to the method without departing from the invention. It is intended to cover in the appended claims, all such modifications and equivalents as fall within the true spirit and scope of the method of our invention.

We claim:

1. A method of selectively sensing the quantity of methane gas in an oxygen containing gas stream, which comprises the steps of:
   providing a platinum catalyst;
   providing a palladium catalyst;
   electrically interconnecting said platinum and said palladium catalysts so as to obtain an electrical output reading therefrom;
   heating said electrically interconnected catalysts to a temperature in a range from 350–450° C. whereby a reference electrical output reading is obtained therefrom;
   passing the gas stream over said electrically interconnected catalysts, methane gas contained in the gas stream being oxidized only by said palladium catalyst while all other oxidizable components of the gas stream being oxidized by both catalysts, whereby said palladium catalyst will be heated to a temperature proportionately higher than said platinum catalyst based on the percentage of methane gas contained in the gas stream;
   obtaining a sample measuring electrical output reading from said electrically interconnected catalysts while said suspected methane containing gas stream is passing thereover; and
   comparing said sample measuring electrical output reading to said reference electrical output reading to determine said percentage of methane gas contained in the gas stream.

2. The method of claim 1, wherein said platinum catalyst is coated on a thermistor, wherein said palladium catalyst is coated on a thermistor, and wherein said two catalyst coated thermistors are electrically interconnected.

3. A method of selectively sensing the quantity of methane gas in an oxygen containing gas stream, which comprises the steps of:
   providing a platinum catalyst;
   providing a palladium catalyst;
   interconnecting said platinum and said palladium catalysts in series electrical connection;
   applying an electrical potential to said interconnected catalysts so as to obtain an electrical output reading therefrom;
   heating said electrically interconnected catalysts to a temperature in a range from 350–450° C. whereby a reference electrical output reading is obtained therefrom;
   passing the gas stream over said interconnected catalysts, methane gas contained in the gas stream being oxidized only by said palladium catalyst while all other oxidizable components of the gas stream being oxidized by both catalysts, whereby said palladium catalyst will be heated to a temperature proportionately higher than said platinum catalyst based on the percentage of methane gas contained in the gas stream;
   obtaining a sample measuring electrical output reading from said electrically interconnected catalysts while said suspected methane containing gas stream is passing thereover; and
   comparing said sample measuring electrical output reading to said reference electrical output reading to determine said percentage of methane gas contained in the gas stream.

4. The method of claim 3, wherein said platinum catalyst is coated on a thermistor, wherein said palladium catalyst is coated on a thermistor, and wherein said two catalyst coated thermistors are electrically interconnected.

5. A method of selectively sensing the quantity of methane gas in an oxygen containing gas stream, which comprises the steps of:
   providing a high thermoelectric material having a high temperature resistance;
   coating a first area of said high thermoelectric material with a platinum catalyst;
   coating a second area of said high thermoelectric material spaced from and separate from said first area with a palladium catalyst;
   electrically interconnecting said platinum and said palladium catalysts on said thermoelectric material so that an electrical output-reading is obtainable therefrom;
   heating said electrically interconnected catalysts to a temperature in a range from 350°–450° C. whereby a reference electrical output reading is obtained therefrom;
   passing the gas stream over said electrically interconnected catalysts, methane gas contained in the gas stream being oxidized only by said palladium catalyst while all other oxidizable components of the gas stream being oxidized by both catalysts, whereby said palladium catalyst will be heated to a temperature proportionately higher than said platinum catalyst based on the percentage of methane gas contained in the gas stream;
   obtaining a sample measuring electrical output reading from said electrically interconnected catalysts while said suspected methane containing gas stream is passing thereover;
   comparing said sample measuring electrical output reading to said reference electrical output reading to determine said percentage of methane gas contained in the gas stream.

* * * * *